(12) United States Patent
Wei et al.

(10) Patent No.: US 10,905,518 B2
(45) Date of Patent: Feb. 2, 2021

(54) METHODS AND SYSTEMS FOR REAL-TIME SURGICAL PROCEDURE ASSISTANCE USING AN ELECTRONIC ORGAN MAP

(75) Inventors: Guo-Qing Wei, Plainsboro, NJ (US); Jian-Zhong Qian, Princeton Junction, NJ (US); Cheng-Chung Liang, West Windsor, NJ (US); Xiaolan Zeng, Princeton, NJ (US); Li Fan, Belle Mead, NJ (US); Feng Ma, Cherry Hill, NJ (US)

(73) Assignees: EDDA TECHNOLOGY, INC., Princeton, NJ (US); EDDA TECHNOLOGY MEDICAL SOLUTIONS (SUZHOU) LTD., Suzhou (CN)

( * ) Notice: Subject to any disclaimer, the term of this patent is extended or adjusted under 35 U.S.C. 154(b) by 862 days.

(21) Appl. No.: 13/180,452

(22) Filed: Jul. 11, 2011

(65) Prior Publication Data

US 2012/0029387 A1    Feb. 2, 2012

Related U.S. Application Data

(60) Provisional application No. 61/363,049, filed on Jul. 9, 2010.

(51) Int. Cl.
*A61B 5/107* (2006.01)
*A61B 90/00* (2016.01)
(Continued)

(52) U.S. Cl.
CPC .............. *A61B 90/36* (2016.02); *A61B 34/20* (2016.02); *A61B 2034/105* (2016.02); *A61B 2090/366* (2016.02); *A61B 2090/378* (2016.02)

(58) Field of Classification Search
CPC ...... A61B 34/10; A61B 2034/101–104; A61B 2034/107–108; A61B 2034/105; A61B 2090/366–368; A61B 90/37; A61B 8/085
(Continued)

(56) References Cited

U.S. PATENT DOCUMENTS

| 6,226,542 B1 | 5/2001 | Reisfeld |
| 6,381,485 B1 | 4/2002 | Hunter et al. |

(Continued)

FOREIGN PATENT DOCUMENTS

WO       WO98/24065        6/1998

OTHER PUBLICATIONS

International Search Report dated Nov. 25, 2011 corresponding to PCT/US11/043600.

*Primary Examiner* — Devin B Henson
*Assistant Examiner* — H. Q. Nguyen
(74) *Attorney, Agent, or Firm* — Pillsbury Winthrop Shaw Pittman LLP

(57) ABSTRACT

Methods, systems, and programs for real-time surgical procedure assistance are provided. A first set of 3D poses of the 3D points on the organ may be received. An electronic organ map built for the organ via pre-surgical medical information may be retrieved. A tissue parameter of the organ may be obtained based on the first set of 3D poses and their corresponding 3D poses from the electronic organ map. A deformation transformation of the electronic organ map may be calculated based on the obtained tissue parameter and the first set of 3D poses during the surgical procedure. The deformed electronic organ map may be projected onto the organ with respect to the first set of 3D poses during the surgical procedure.

20 Claims, 16 Drawing Sheets

(51) Int. Cl.
*A61B 34/20* (2016.01)
*A61B 34/10* (2016.01)

(58) Field of Classification Search
USPC .................................................. 600/587, 424
See application file for complete search history.

(56) References Cited

U.S. PATENT DOCUMENTS

| | | | |
|---|---|---|---|
| 7,130,676 | B2 | 10/2006 | Barrick |
| 7,398,116 | B2 | 7/2008 | Edwards |
| 2002/0077533 | A1* | 6/2002 | Bieger .................. A61B 90/36 600/300 |
| 2003/0164172 | A1* | 9/2003 | Chumas ................ A61B 90/13 128/898 |
| 2003/0220557 | A1 | 11/2003 | Cleary et al. |
| 2004/0059216 | A1 | 3/2004 | Vetter et al. |
| 2005/0182319 | A1 | 8/2005 | Glossop |
| 2005/0234332 | A1* | 10/2005 | Murphy ................ A61B 5/4528 600/426 |
| 2006/0058604 | A1* | 3/2006 | Avinash ................ A61B 5/06 600/407 |
| 2007/0225550 | A1* | 9/2007 | Gattani ................ A61B 90/36 600/101 |
| 2008/0071292 | A1* | 3/2008 | Rich .................... A61B 90/36 606/130 |
| 2008/0095422 | A1* | 4/2008 | Suri .................... G06K 9/6206 382/131 |
| 2009/0088634 | A1 | 4/2009 | Zhao |
| 2009/0088773 | A1 | 4/2009 | Zhao |
| 2010/0268067 | A1* | 10/2010 | Razzaque ............. A61B 34/10 600/424 |

* cited by examiner

METHODS AND SYSTEMS FOR REAL-TIME SURGICAL PROCEDURE ASSISTANCE USING AN ELECTRONIC ORGAN MAP

CROSS-REFERENCE TO RELATED APPLICATIONS

The present application claims priority to U.S. Provisional Application Ser. No. 61/363,049 filed Jul. 9, 2010 entitled, "METHODS FOR REAL TIME POSITIONING OF SURGICAL INSTRUMENTS IN SOFT TISSUE HUMAN ORGAN AND A NAVIGATION SYSTEM FOR REAL TIME FUNCTIONAL ANALYSIS USING AN ELECTRONIC ORGAN MAP," which is incorporated herein by reference in its entirety.

BACKGROUND

1. Technical Field

The present teaching relates generally to methods, systems, and programming for surgical procedure assistance. In particular, the present teaching relates to methods, systems, and programming for real-time surgical procedure assistance using an electronic organ map.

2. Discussion of Technical Background

In image guided surgery (IGS) systems, fiducial-mark-based registration is the most widely used registration method. This type of registration methods are widely applied in IGS in brain surgery, ENT (ear, nose, and throat) surgery and other types of bone surgeries. However, for soft-tissue organs, such as liver, lung, kidney and others, the IGS system is not widely adopted yet. One of the major difficulties in the IGS for soft-tissue organ registration is the non-rigid motion of human soft-tissue organ during surgery. The 3D soft-tissue motion is very complicated to model mathematically and very difficult to be determined in real-time.

Furthermore, most current navigations system provide only positional guide of the surgical instrument. This may suffice for surgeries like tumor removal in the brain, where surgeons are mostly interested in how to get to the tumor location. In soft-tissue organ surgery, such as liver transplantation or lesion resection, the functional prediction of the remnant organ is vital during surgery. Due to the deformation of the organ during surgery, the preplanned surgical path may not be followed exactly. So it is highly desirable to quantify such deviations and predict the functional and volumetric measurement of the remnant organ during surgical operations.

In order for surgeons to see both the actual organ and the pre-planned surgical path and vital anatomies at the same time, current surgical navigation systems use augmented realty technologies to merge the electronic organ map with the actual organ. That requires users to wear special electronic glasses. It is desirable that user may see both the actual organ and pre-planned surgery paths and interested anatomies inside the organ without wearing special glasses. Therefore, there is a need to provide methods, systems, and programming for real-time surgical procedure assistance.

SUMMARY

The teachings disclosed herein relate to methods, systems, and programming for surgical procedure assistance using an electronic organ map. More particularly, the present teaching relates to methods, systems, and programming for real-time surgical procedure assistance using an electronic organ map.

In one example, a method, implemented on a computer having at least one processor, a storage, and a communication platform for real-time surgical procedure assistance is provided. First, a first set of 3D poses of the 3D points on the organ may be received. The first set of 3D poses represents positions and orientations of the corresponding 3D positions tracked in real-time via a plurality of sensors placed with respect to the organ to which a surgical procedure is applied. It may also represent positions and orientations of a set of landmarks interactively picked during surgery. It may also present positions and orientations of a set of landmarks automatically suggested by computer and confirmed by users during surgery. 3D poses of such points may be obtained by attaching sensors to the points or by manually touching the points using the tip of a position collection tool. The first set of 3D poses can change over time during the surgical procedure. An electronic organ map built for the organ via pre-surgical medical information may be retrieved. A tissue parameter of the organ then may be obtained based on the first set of 3D poses and their corresponding 3D poses from the electronic organ map. A deformation transformation of the electronic organ map may be calculated based on the obtained tissue parameter and the first set of 3D poses of the plurality of sensors during the surgical procedure. The deformed electronic organ map may be projected onto the organ with respect to the first set of 3D poses during the surgical procedure.

In another example, a method, implemented on a computer having at least one processor, a storage, and a communication platform for real-time surgical procedure assistance is provided. First, a first set of 3D poses of the 3D points on the organ may be received. The first set of 3D poses represents positions and orientations of the corresponding 3D positions tracked in real-time via a plurality of sensors placed with respect to the organ to which a surgical procedure is applied. The first set of 3D poses can change over time during the surgical procedure. It may also represent positions and orientations of a set of landmarks interactively picked during surgery. It may also present positions and orientations of a set of landmarks automatically suggested by computer and confirmed by users during surgery. 3D poses of such points may be obtained by attaching sensors to the points or by manually touching the points using the tip of a position collection tool. An electronic organ map built for the organ via pre-surgical medical information may be retrieved. A second set of 3D poses from the electronic organ map that correspond to the first set of 3D poses then may be identified by registering each of the 3D points in the first set of 3D poses with a corresponding 3D point from the electronic organ map. A deformation transformation of the electronic organ map may be calculated based on the registration between the first set of 3D poses and the second set of 3D poses. Information related to at least one dynamic 3D pose of a surgical instrument which moves during the surgical procedure may also be received. Predictive functional and volumetric measurements of the organ then may be computed based on a predicted movement of the surgical instrument in accordance with the at least one dynamic 3D pose of the surgical instrument. One or more dynamically changing features associated with one or more pre-determined anatomy-based-alerts may be automatically computed based on the deformed electronic organ map and the at least one dynamic 3D poses of the surgical instrument. Optionally, the one or more dynamically changing features may be shown on a display to facilitate the surgeon's operation.

In a different example, a system for real-time surgical procedure assistance is provided. The system includes a tracking unit, an electronic organ map, a registration unit, and an electronic organ map projection unit. The tracking unit is configured to receive a first set of 3D poses representing positions and orientations of corresponding 3D points tracked in real-time via a plurality of sensors placed with respect to an organ to which a surgical procedure is applied, wherein the first set of 3D poses can change over time during the surgical procedure. The first set of 3D points may include a set of landmarks interactively picked during surgery. It may also include another set of landmarks automatically suggested by computer and confirmed by users during surgery. 3D poses of such points may be obtained by attaching sensors to the points or by manually touching the points using the tip of a position collection tool. The electronic organ map is built for the organ via pre-surgical medical information. The registration unit is operatively coupled to the tracking unit and the electronic organ map and is configured to obtain a tissue parameter of the organ based on the first set of 3D poses and their corresponding 3D poses from the electronic organ map. The registration unit is also configured to compute a deformation transformation of the electronic organ map based on the obtained tissue parameter and the first set of 3D poses of the plurality of sensors during the surgical procedure. The electronic organ map projection unit is operatively coupled to the electronic organ map and is configured to project the deformed electronic organ map onto the organ with respect to the first set of 3D poses during the surgical procedure.

In still a different example, a system for real-time surgical procedure assistance is provided. The system includes a tracking unit, an electronic organ map, a registration unit, a real-time organ function prediction unit, a real-time anatomy-on-alert monitoring unit, and a display. The tracking unit is configured to receive a first set of 3D poses representing positions and orientations of corresponding 3D points tracked in real-time via a plurality of sensors placed with respect to an organ to which a surgical procedure is applied, wherein the first set of 3D poses can change over time during the surgical procedure. The tracking unit is also configured to receive information related to at least one dynamic 3D pose of a surgical instrument which moves during the surgical procedure. The electronic organ map is built for the organ via pre-surgical medical information. The registration unit is operatively coupled to the tracking unit and the electronic organ map and is configured to identify a second set of 3D poses from the electronic organ map that correspond to the first set of 3D poses by registering each of the 3D points in the first set of 3D poses with a corresponding 3D point from the electronic organ map. The registration unit is also configured to compute a deformation transformation of the electronic organ map based on the registration between the first set of 3D poses and the second set of 3D poses. The real-time organ function prediction unit is operatively coupled to the electronic organ map and is configured to compute predictive functional and volumetric measurements of the organ based on a predicted movement of the surgical instrument in accordance with the at least one dynamic 3D pose of the surgical instrument. The real-time anatomy-on-alert monitoring unit is operatively coupled to the electronic organ map and configured to compute, automatically, one or more dynamically changing features associated with one or more pre-determined anatomy-based-alerts based on the deformed electronic organ map and the at least one dynamic 3D poses of the surgical instrument. The display is configured to display the one or more dynamically changing features.

Other concepts relate to software for implementing the real-time surgical procedure assistance. A software product, in accord with this concept, includes at least one machine-readable non-transitory medium and information carried by the medium. The information carried by the medium may be executable program code data regarding parameters in association with a request or operational parameters, such as information related to a user, a request, or a social group, etc.

In one example, a machine readable and non-transitory medium having information recorded thereon for real-time surgical procedure assistance, wherein the information, when read by the machine, causes the machine to perform a series of steps. First, a first set of 3D poses of the 3D points on the organ may be received. The first set of 3D poses represents positions and orientations of the corresponding 3D positions tracked in real-time via a plurality of sensors placed with respect to the organ to which a surgical procedure is applied. The first set of 3D poses can change over time during the surgical procedure. An electronic organ map built for the organ via pre-surgical medical information may be retrieved. A tissue parameter of the organ then may be obtained based on the first set of 3D poses and their corresponding 3D poses from the electronic organ map. A deformation transformation of the electronic organ map may be calculated based on the obtained tissue parameter and the first set of 3D poses of the plurality of sensors during the surgical procedure. The deformed electronic organ map may be projected onto the organ with respect to the first set of 3D poses during the surgical procedure.

In another example, a machine readable and non-transitory medium having information recorded thereon for real-time surgical procedure assistance, wherein the information, when read by the machine, causes the machine to perform a series of steps. First, a first set of 3D poses of the 3D points on the organ may be received. The first set of 3D poses represents positions and orientations of the corresponding 3D positions tracked in real-time via a plurality of sensors placed with respect to the organ to which a surgical procedure is applied. The first set of 3D poses can change over time during the surgical procedure. An electronic organ map built for the organ via pre-surgical medical information may be retrieved. A second set of 3D poses from the electronic organ map that correspond to the first set of 3D poses then may be identified by registering each of the 3D points in the first set of 3D poses with a corresponding 3D point from the electronic organ map. A deformation transformation of the electronic organ map may be calculated based on the registration between the first set of 3D poses and the second set of 3D poses. Information related to at least one dynamic 3D pose of a surgical instrument which moves during the surgical procedure may also be received. Predictive functional and volumetric measurements of the organ then may be computed based on a predicted movement of the surgical instrument in accordance with the at least one dynamic 3D pose of the surgical instrument. One or more dynamically changing features associated with one or more pre-determined anatomy-based-alerts may be automatically computed based on the deformed electronic organ map and the at least one dynamic 3D poses of the surgical instrument. Optionally, the one or more dynamically changing features may be shown on a display to facilitate the surgeon's operation.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

Figure 1A:
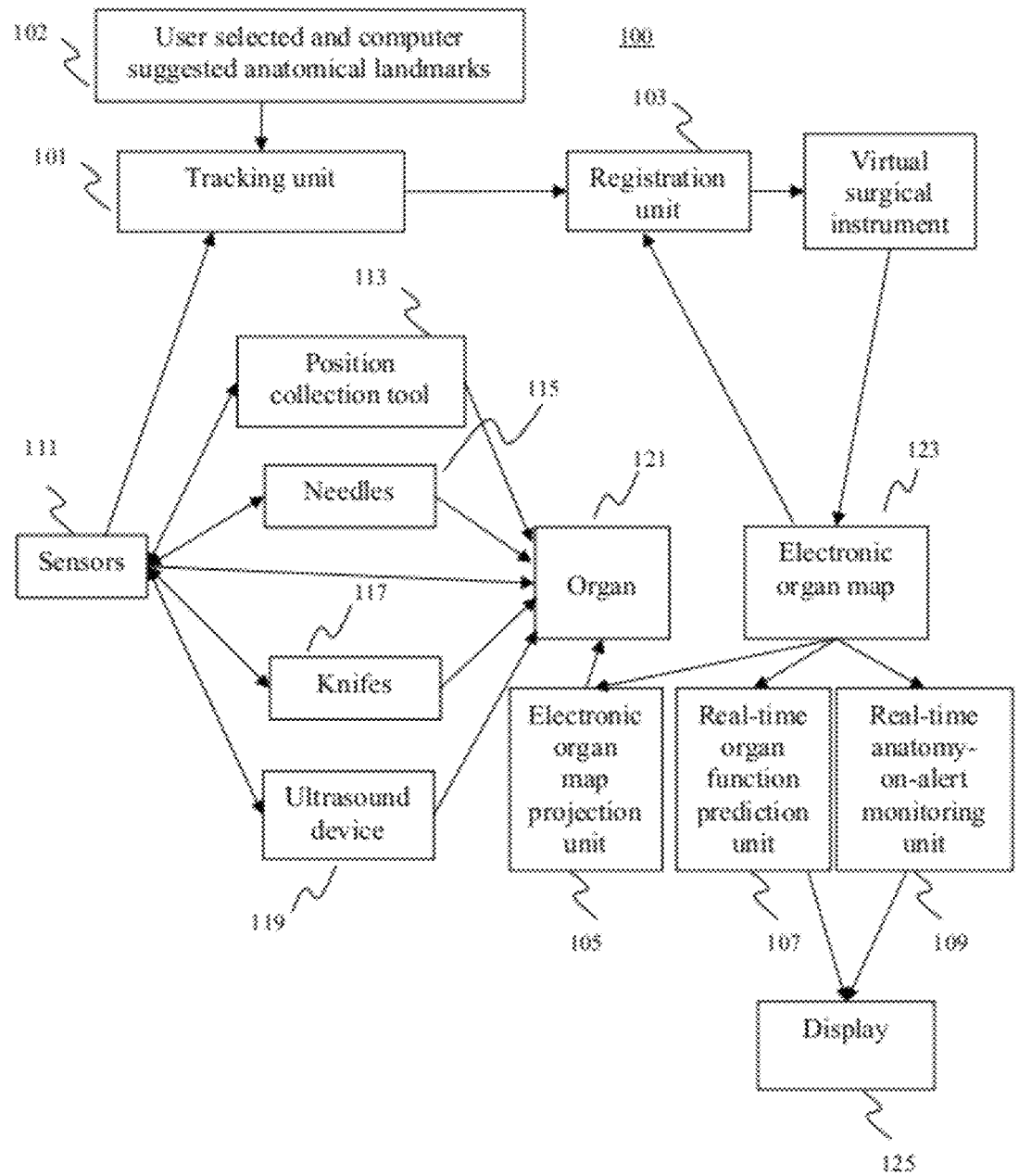
FIG. 1(a) depicts an exemplary system diagram for a real-time surgical procedure assistance system, according to an embodiment of the present teaching.

FIG. 1(a) shows an exemplary system diagram for a real-time surgical procedure assistance system 100 for human soft-tissue organs 121, according to an embodiment of the present teaching. In this example, the exemplary system 100 includes a tracking unit 101, a registration unit 103, an electronic organ map projection unit 105, a real-time organ function prediction unit 107, and a real-time anatomy-on-alert monitoring unit 109. The tracking unit 101 may obtain three-dimensional (3D) pose (position and orientation) information of a set of sensors 111. The sensors 111 may be, for example optical sensors, magnetic sensors, or any other suitable sensors that are capable of detecting their 3D positions and orientations. The sensors 111 may be attached to different instruments, such as but not limited to, a position collection tool 113, needles 115, surgical knives 117, and ultrasound devices 119. The sensors 111 may also be directly attached to the organ. The tracking unit 101 may also receive information related to at least one dynamic 3D pose of a surgical instrument that moves during the surgical procedure, which can be detected via one or more sensors attached to the surgical instrument, such as the surgical knives 117 and ultrasound devices 119. The dynamic 3D pose of the surgical instrument changes when the surgical instrument is in motion during the surgical procedure. The tracking unit 101 may also receive 3D pose information of a set of user re-positioned sensors on exposed anatomical landmarks during surgery. Such anatomical landmarks 102 may either be user selected or computer suggested with user confirmation.

The registration unit 103's input may be the 3D pose information of the sensors 111 from the tracking unit 101 and the corresponding 3D points from an electronic organ map 123 (E-map). The registration unit 103's input may also include 3D pose information of a set of user-selected anatomical landmarks or a set of computer-suggested anatomical landmarks 102. By placing the tip of a position collection tool or a sensor-attached surgical instrument on such anatomical landmarks 102, the 3D pose information may be obtained. In other words, the 3D points on the surface of the organ and inside the organ may be dynamically re-assigned during the surgery procedure. The electronic organ map 123 may be obtained from one or more pre-surgical scannings of the patient, such as CT scans, MRI scans, ultrasound scans, or any other suitable scanning. The electronic organ map 123 may contain organ segmentation and segmentation of other anatomies, such as vascular structures. The electronic organ map 123 may also contain pre-surgical planning results, such as surgical paths. The electronic organ map 123 may be projected by the electronic organ map projection unit 105 onto the actual organ 121 during the surgical procedure to indicate locations of invisible anatomies, such as vessels inside the organ 121, preplanned surgical paths, or any other invisible anatomies. The real-time organ function prediction unit 107 may compute predictive functional and volumetric measurements of the organ based on a predicted movement of the surgical instrument in accordance with the at least one dynamic 3D pose of the surgical instrument. For example, the real-time organ function prediction unit 107 may predict the organ function based on the dynamic 3D pose of surgical instruments and a predicted cutting during surgery. The real-time anatomy-on-alert monitoring unit 109 may compute, automatically, one or more dynamically changing features associated with one or more pre-determined anatomy-based-alerts based on the deformed electronic organ map and the at least one dynamic 3D poses of the surgical instrument. For example, the real-time anatomy-on-alert monitoring unit 109 may monitor pre-selected vital anatomies, such as arteries, based on proximity measurement to the surgical instruments. The real-time anatomy-on-alert monitoring unit 109 may also monitor deviations of the actual surgical path to the planned one. One or more dynamically changing features associated with the anatomy-on-alerts during the surgical procedure may be displayed on a display 125 for the surgeons' reference.

The placement of sensors 111 may not be limited to one organ 121. The sensors 111 may be placed on multiple organs at the same time. In one embodiment of the present teaching, the soft-tissue organ 121 may be human liver organ. The position collection tool 113 is a tool used for collecting a set of 3D points which may have one or more sensors attached. After calibration of the sensor and the position collection tool 113, 3D pose of the position collection tool 113's tip may be obtained at any user's placed points. Similar calibrations may be performed for needles 115, surgical knives 117, and ultrasound devices 119. The sensors 111 may also be directly fixed on the surface of the organ 121 or inside the organ 121. The sensors 111 may be dynamically re-positioned during surgery. For example, as surgery progresses, some important anatomical landmarks may show up. The sensors 111 may then be attached onto the exposed anatomical landmarks, so that such anatomical landmarks may be tracked and monitored during surgery.

Figure 1B:
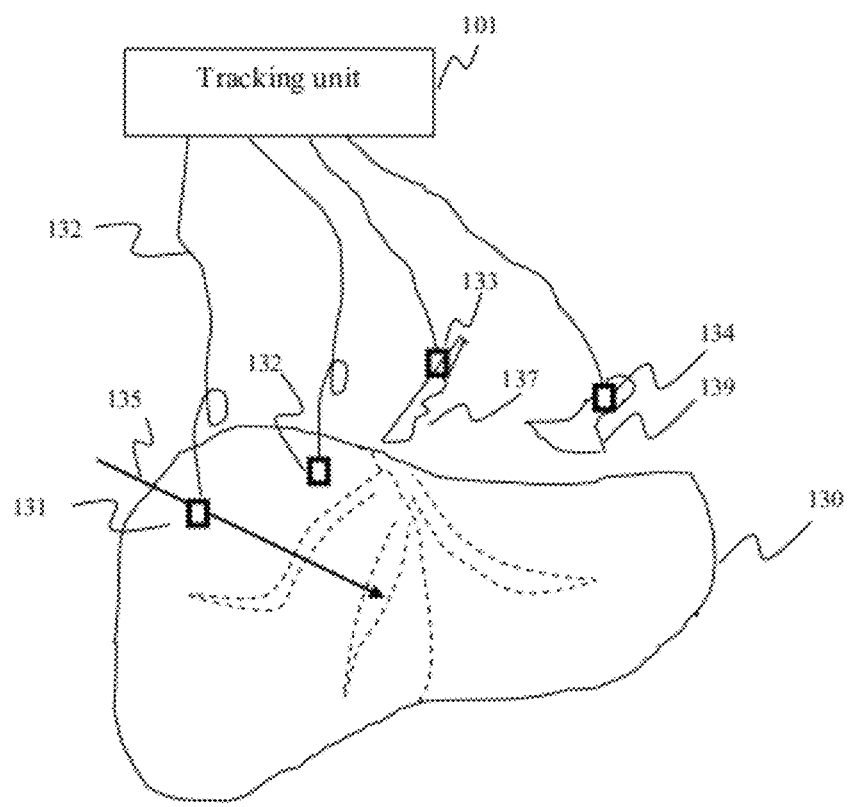
FIG. 1(b) illustrates an exemplary sensor placement on a soft-tissue organ, according to an embodiment of the present teaching.

FIG. 1(*b*) illustrates an exemplary sensor placement on a human liver organ 130, according to an embodiment of the present teaching. In this example, a set of sensors 131, 132, 133, 134 are, respectively, attached to a needle 131, the surface of the liver 130, the handle of a knife 133, and the probe of an ultrasound device 139. The tracking unit 101 is connected to the sensors 131, 132, 133, 134 through electric wires 132 to track the 3D pose of each 3D point on or inside the liver 130 and on the surgical instrument in real-time during the surgical procedure.

Figure 2:
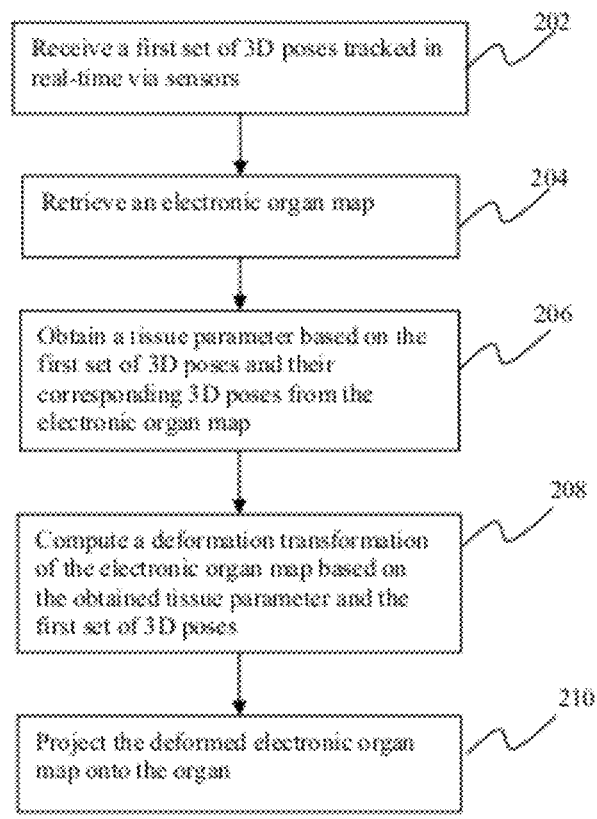
FIG. 2 is a flowchart of an exemplary process of a real-time surgical procedure assistance system, according to an embodiment of the present teaching.

FIG. 2 is a flowchart of an exemplary process of the real-time surgical procedure assistance system 100, according to an embodiment of the presenting teaching. At step 202, a first set of 3D poses of the 3D points on the organ may be received. The first set of 3D poses represents positions and orientations of the corresponding 3D positions tracked in real-time via a plurality of sensors placed with respect to the organ to which a surgical procedure is applied. The first set of 3D poses can change over time during the surgical procedure. At step 204, an electronic organ map built for the organ via pre-surgical medical information may be retrieved. Proceeding to step 206, a tissue parameter of the organ may be obtained based on the first set of 3D poses and their corresponding 3D poses from the electronic organ map. At step 208, a deformation transformation of the electronic organ map may be calculated based on the obtained tissue parameter and the first set of 3D poses of the plurality of sensors during the surgical procedure. At step 210, the deformed electronic organ map may be projected onto the organ with respect to the first set of 3D poses during the surgical procedure to help the surgeon see the invisible anatomies and/or preplanned surgical paths.

Figure 3:
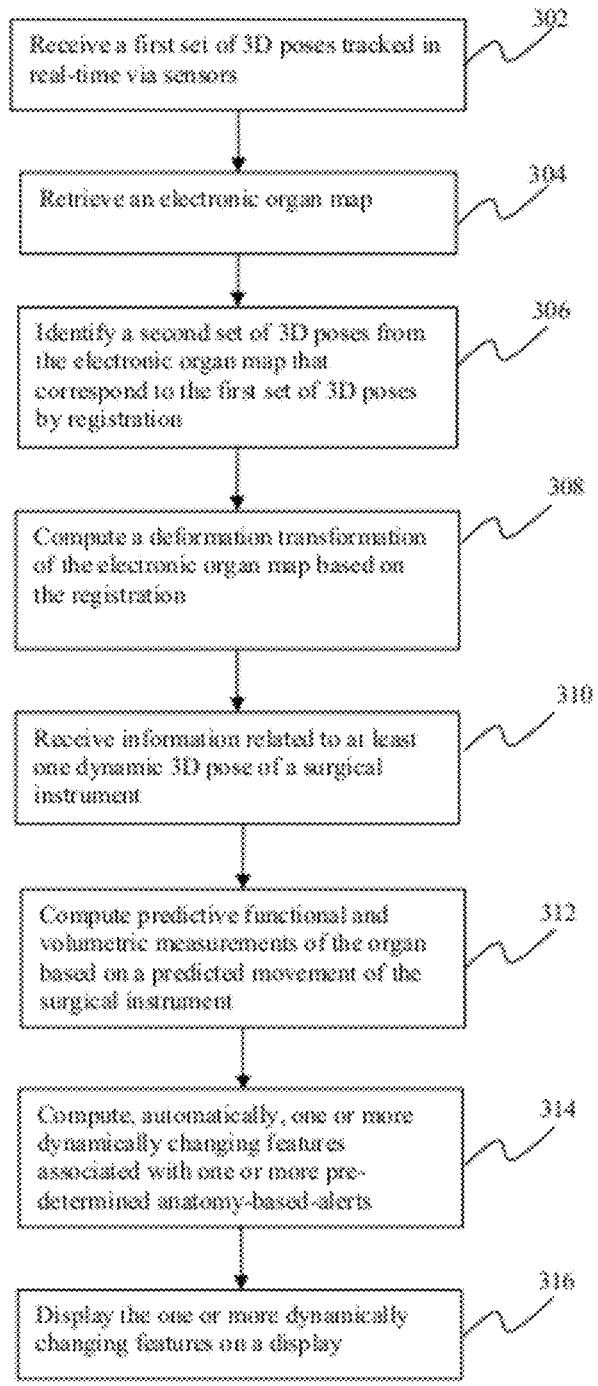
FIG. 3 is a flowchart of another exemplary process of a real-time surgical procedure assistance system, according to an embodiment of the present teaching.

FIG. 3 is a flowchart of another exemplary process of the real-time surgical procedure assistance system 100, according to an embodiment of the presenting teaching. At step 302, a first set of 3D poses of the 3D points on the organ may be received. The first set of 3D poses represents positions and orientations of the corresponding 3D positions tracked in real-time via a plurality of sensors placed with respect to the organ to which a surgical procedure is applied. The first set of 3D poses can change over time during the surgical procedure. At step 304, an electronic organ map built for the organ via pre-surgical medical information may be retrieved. Proceeding to step 306, a second set of 3D poses from the electronic organ map that correspond to the first set of 3D poses may be identified. Step 306 may be performed by registering each of the 3D points in the first set of 3D poses with a corresponding 3D point from the electronic organ map. At step 308, a deformation transformation of the electronic organ map may be calculated based on the registration between the first set of 3D poses and the second set of 3D poses. At step 310, information related to at least one dynamic 3D pose of a surgical instrument which moves during the surgical procedure may be received. Proceeding to step 312, predictive functional and volumetric measurements of the organ may be computed based on a predicted movement of the surgical instrument in accordance with the at least one dynamic 3D pose of the surgical instrument. At step 314, one or more dynamically changing features associated with one or more pre-determined anatomy-based-alerts may be automatically computed based on the deformed electronic organ map and the at least one dynamic 3D poses of the surgical instrument. Optionally, at step 316, the one or more dynamically changing features may be shown on a display to facilitate the surgeons' operation. The one or more dynamically changing features include, but are not limited to, a projection of anatomical structure of the organ rendered on the display with respect to the organ, a prediction of the function of the organ, which is dynamically changed with the movement of the surgical instrument during the surgical procedure, and one or more warnings generated based on the at least one dynamic 3D pose of the surgical instrument and the anatomical structure of the organ. As another embodiment of the present teaching, the electronic map may not be deformed in the computation of predictive value of the organ function or in the computation of dynamically changing features. Rather, the position and orientation of the surgical tools may be updated in the electronic organ map according to the deformation transformation.

Figure 4:
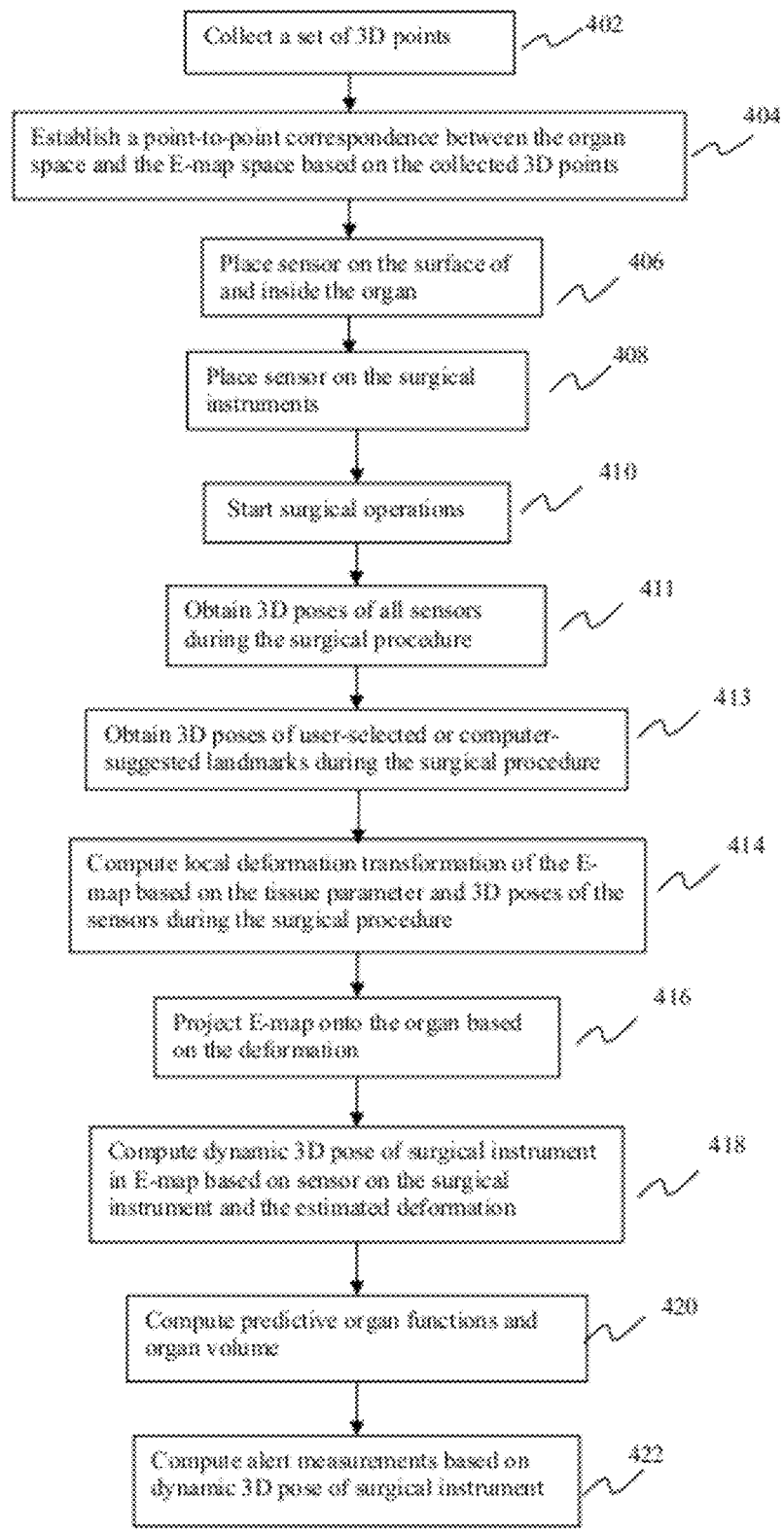
FIG. 4 is a detailed flowchart of an exemplary process of a real-time surgical procedure assistance system, according to an embodiment of the present teaching.

FIG. 4 is a detailed flowchart of an exemplary process of the real-time surgical procedure assistance system 100, according to an embodiment of the present teaching. First, the positions and orientations of a set of 3D points may be collected from the organ surface at step 402. For example, step 402 may be performed by swapping the tip of the position collection tool on the surface or placing it at uniquely identifiable landmarks of the organ. At step 404, a registration may be performed between the collected 3D points and the surface points of the organ in the electronic organ map. Step 404 may establish a correspondence between each point in the organ space and that in the E-map coordinate system. The method of registration may be any suitable methods that register a set of points with a surface, as known in the art. At step 406, sensors may be placed on the surface of the organ and/or inside the organ. The placement of sensors may be based on an analysis of the electronic organ map. For example, the pre-surgical planning may indicate lines of incision on the surface of the organ. Then sensors may be placed in the vicinity of the incision line. At step 408, sensors may be placed on the surgical instruments. At step 410, surgical operations may start. At step 412, 3D poses of some or all of the sensors may be obtained through the tracking unit in real-time during surgery. At step 413, 3D poses of user-selected landmarks or computer suggested landmarks may be obtained. As surgery progresses, user may identify such landmarks for obtaining 3D pose information to improve registration accuracy at interested organ locations. At step 414, based on the 3D poses of the sensors on the organ and/or inside the organ, a deformation transformation may be computed based on the estimation of a tissue parameter. At step 416, the electronic organ map may be deformed according to the estimated deformation transformation and then projected onto the actual organ surface. With such a projection, invisible anatomies or preplanned surgical paths may become visible on the actual organ. This may help surgeons localize preplanned surgical incision lines or see invisible vascular structures inside the organ. At step 418, based on at least one dynamic 3D pose of the sensor attached on the surgical instruments and the estimated deformation transformation, the surgical instrument's position and orientation in the E-map may be updated. At step 420, based on the updated position and orientation of the surgical instrument in the E-map, one or more dynamically changing features (e.g., predictive surgical effects) may be simulated. Based on that, predicted functional and volumetric measurements of the organ may be computed. At step 422, some alert measurements may be computed based on the current surgical instrument's 3D pose. The measurements may be displayed as colored graphic bars. As an exemplary embodiment of the present teaching, the distance of the surgical instrument to an artery segment may be computed. If the distance falls within a pre-defined threshold, a warning may be issued. The warning may be in the form of a flashing display, a sound, or any other suitable form.

Figure 5A:
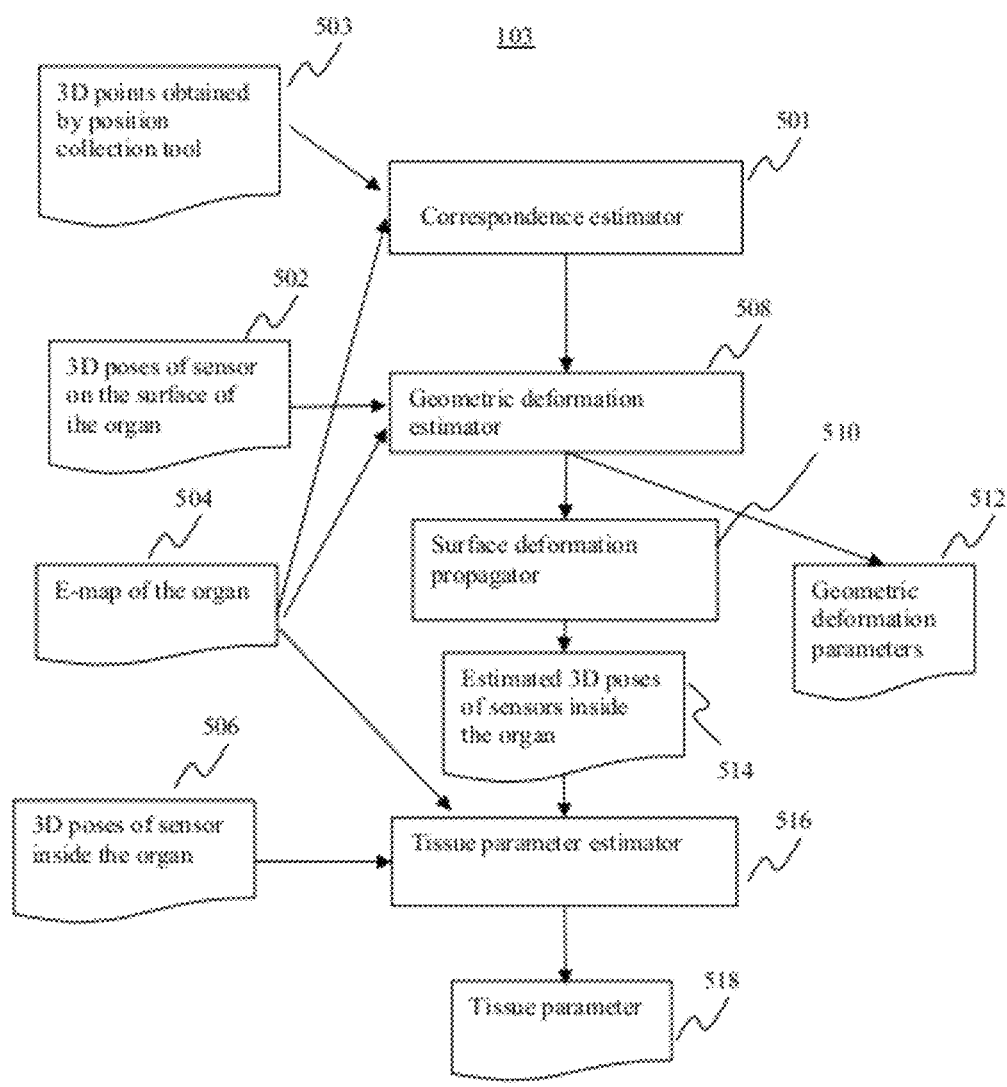
FIG. 5(a) shows an exemplary system diagram of a registration unit, according to an embodiment of the present teaching.

FIG. 5(a) is an exemplary system diagram of the registration unit 103, according to an embodiment of the present teaching. In this example, the registration unit 103 may include a correspondence estimator 501, a geometric deformation estimator 508, a surface deformation propagator 510, and a tissue parameter estimator 516. The correspondence estimator 501 may establish a one-to-one correspondence between the organ space and the E-map space based on the 3D points 503 collected by the position collection tool and the E-map 504. The geometric deformation estimator 508 may take the 3D poses 502 of the sensors on the surface of the organ and the E-map 504 as inputs to estimate the geometric deformation parameters 512. The deformation may propagate to the inside of the organ by the surface deformation propagator 510 to estimate the estimated 3D poses 514 of the sensors inside the organ. The actual 3D poses 506 of the sensors inside the organ may be used to estimate the tissue parameter 518 by the tissue parameter estimator 516.

Figure 5B:
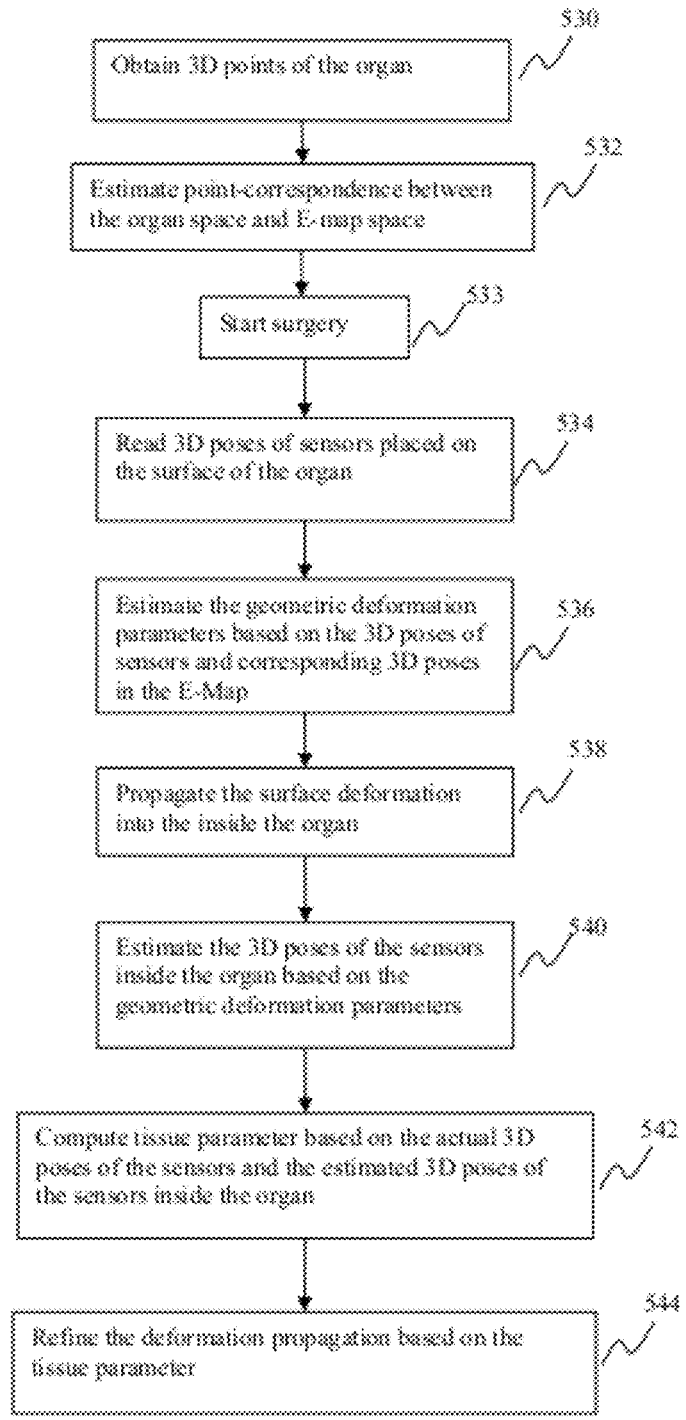
FIG. 5(b) is a flowchart of an exemplary process of the registration unit; according to an embodiment of the present teaching.
Figure 5E:
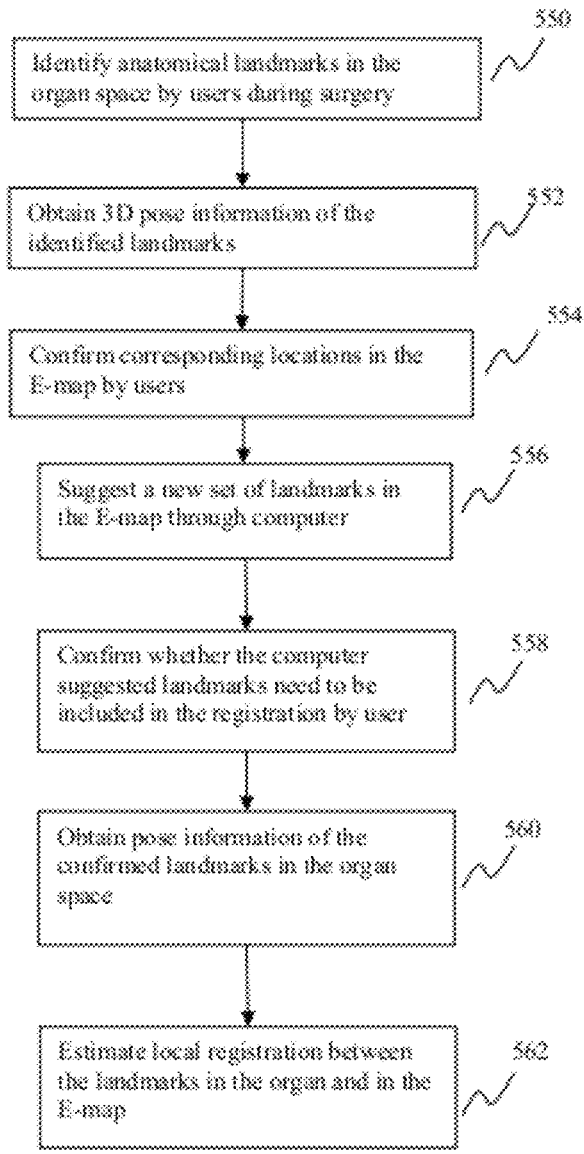
FIG. 5(c) is a flowchart of another exemplary process of the registration unit; according to an embodiment of the present teaching.

FIG. 5(b) is a flow chart of an exemplary process of the registration unit 103 in FIG. 5(a), according to an embodiment of the present teaching. First, positions and orientations of some 3D points on the surface of the organ may be collected by the position collection tool at step 530. At step 532, a one-to-one correspondence between the organ space and the E-map space may be established. Surgery may be started at step 533. Then 3D poses of the sensors placed on the surface of the organ may be obtained at step 534. At step 536, one or more geometric deformation parameters may be estimated. The geometric deformation parameters describe the surface deformation between the actual organ surface and the organ surface in the E-map. The surface deformation may then be propagated into the inside of the organ at step 538. Based on the propagated deformation, the sensors' estimated 3D poses inside the organ may be obtained at step 540. Based on the estimated sensor 3D poses and the actual sensor 3D poses, a tissue parameter may be estimated at step 544. The deformation propagation may be refined at step 544 based on the tissue parameter.

The estimation may be performed as follows, according to one embodiment of the present teaching. Suppose W represents the geometric deformation parameters, X represents the 3D poses of the sensors inside the organ before surgery is started. Based on the geometric deformation propagation, the estimated 3D poses of the sensors may be predicted as $X2=f(X, W, m)$, where m is a tissue parameter, $f(X, W, m)$ is a deformation function, such as a Spline function. Suppose Y is the actual 3D poses of the sensors inside the organ. Then the tissue parameter m may be estimated as the minimization of $\|Y-f(X, W, m)\|$, where $\|\cdot\|$ is an Euclidean distance operator. It is understood that other suitable approaches for estimating the tissue-deformation parameter may be applied in other examples.

FIG. 5(c) is a flow chart of another exemplary process of the registration unit 103 in FIG. 5(a), according to an embodiment of the present teaching. During surgery, a user such as the surgeon may identify, at step 550, additional anatomical landmarks that may be become visible after surgical cutting. Sensors may be attached to such landmarks for real-time tracking of their poses. The user may also use surgical instruments to obtain the 3D pose information of such landmarks, at step 552, by touching the landmarks using the surgical instrument tip. At step 554, the user may confirm the correspondence of such anatomical landmarks in the E-map by clicking on a corresponding point in the E-map. At step 556, more anatomical landmarks may be suggested by a computer in the E-map. The criteria used by computer in suggesting landmarks may be based on proximity measure of the suggested anatomical landmarks to the user-identified anatomical landmarks and saliency measure of the suggested anatomical landmarks. Anatomical landmarks that are closer to the user-selected anatomical landmarks are more likely to be suggested by the computer. Saliency may indicate a uniqueness measure of the anatomical landmark. For example, branching point of vessels are more salient than non-branching points. More salient anatomical landmarks are more likely to be suggested by the computer. At step 558, the user may confirm whether the computer suggested anatomical landmarks need to be included in the registration. At step 560, 3D pose information of computer suggested anatomical landmarks may be obtained, in a similar way as step 552. In other words, the 3D points on the surface of the organ and inside the organ may be dynamically re-assigned during the surgery procedure. At step 562, registration between the organ space and the E-map space may be performed based on the user-identified and computer suggested anatomical landmarks. Since anatomical landmarks may be picked around the vicinity of surgical areas, registration accuracy may be higher around the surgical area. In that sense, the registration is local.

Figure 6A:
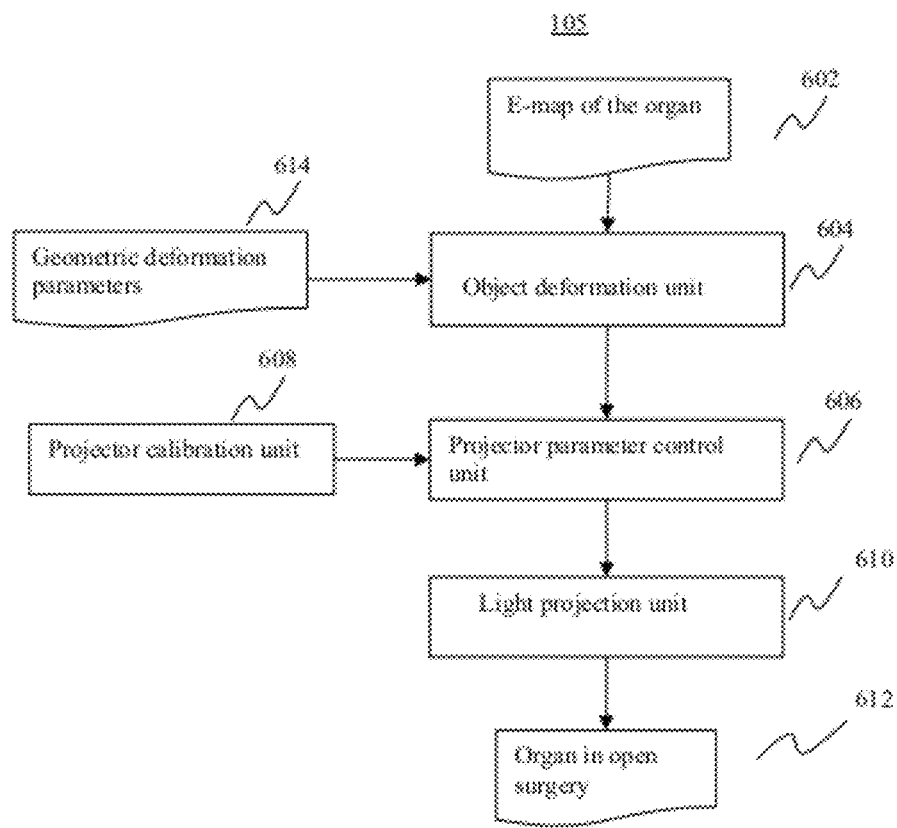
FIG. 6(a) is an exemplary system diagram of an electronic map projection unit, according to an embodiment of the present teaching.

FIG. 6(a) is an exemplary system diagram of the electronic organ map projection unit 105, according to an embodiment of the present teaching. In this example, the electronic organ map projection unit 105 may include an object deformation unit 604, a projector calibration unit 608, a projector parameter control unit 606, and a light projection unit 610. The object deformation unit 604 may deform the E-map 602 based on the geometric deformation parameters 614. The projector calibration unit 608 may calibrate the coordinate transformation between the projector space and the E-map space. This transformation may be used to control the projector's parameters by the projector parameter control unit 606. The light projection unit 610 may project the deformed E-map onto the actual organ 612 during the surgical procedure.

Figure 6B:
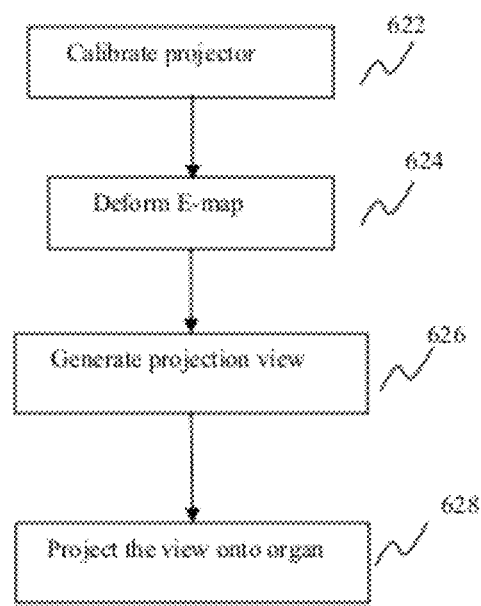
FIG. 6(b) is a flowchart of an exemplary process of the electronic map projection unit, according to an embodiment of the present teaching.

FIG. 6(b) is a flowchart of an exemplary process of the electronic organ map projection unit 105 in FIG. 6(a), according to an embodiment of the present teaching. At step 622, the transformation between the projector space and the E-map space may be calibrated. At step 624, the E-map may be deformed based on the estimated geometric deformation parameters. Based on the transformation between the projector space and the E-map space, a projection view may be generated at step 626. This may generate a view that corresponds to viewing the E-map from the angle of the projector. The projector may then project the view onto the organ at step 628.

Figure 7A:
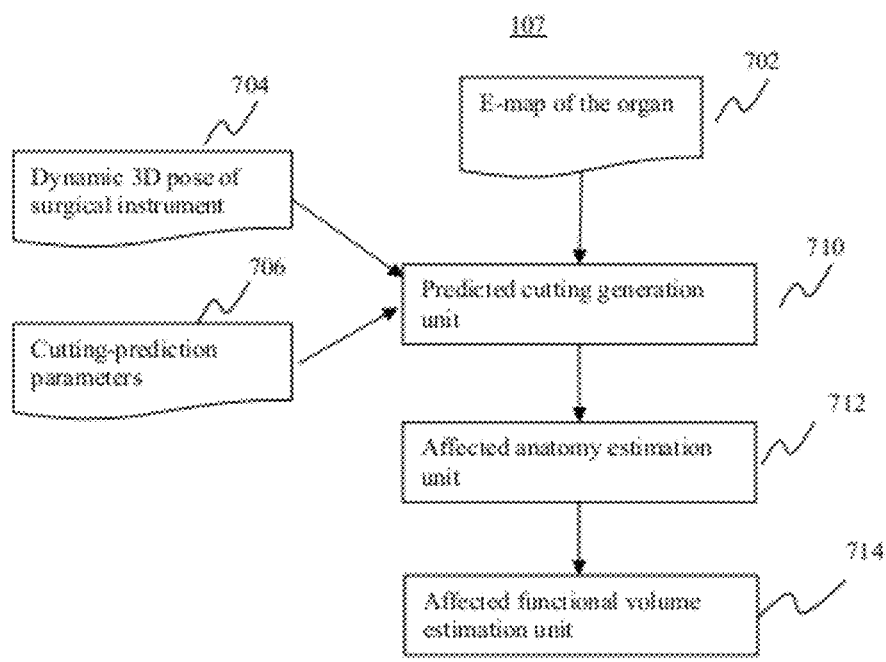
FIG. 7(a) is an exemplary system diagram of a real-time organ function prediction unit, according to an embodiment of the present teaching.

FIG. 7(a) is an exemplary system diagram of the real-time organ function prediction unit 107, according to one embodiment of the present teaching. Based on the dynamic 3D pose of the surgical instrument 704, a predicted cutting generation unit 710 may generate a predicted cutting of the organ (i.e., predicted movement of the surgical instrument) in the E-map 702 of the organ, based on pre-defined cutting-prediction parameters 706. The cutting-prediction parameters may define the extent of a predicted cutting, e.g., how many centimeters a cutting should be predicted. Based on this prediction, an affected anatomy estimation unit 712 may estimate which anatomy may be affected. At step 714, the functional volume of the affected anatomy as well as the remnant functional volume of the organ may be estimated.

Figure 7B:
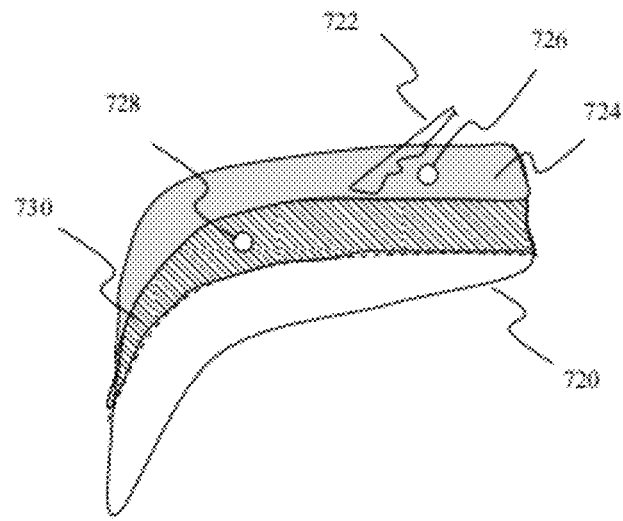
FIG. 7(b) illustrates a cross-sectional view of a predicted surgical cutting of liver organ, according to an embodiment of the present teaching.

FIG. 7(b) illustrates one example of the cross section of a predicted cutting, in which 720 is a cross section of a liver organ, 722 is a surgical knife, 724 is a cut region, 726 is a vessel that is cut. Based on a predefined extent of a predicted cutting, region 730 indicates a predicted cutting, where 728 is an affected anatomy (here it is a hepatic vein). Based on the estimation of the affected anatomies, the functional volume of affected anatomies may be estimated by the affected functional volume estimation unit 714.

Figure 7C:
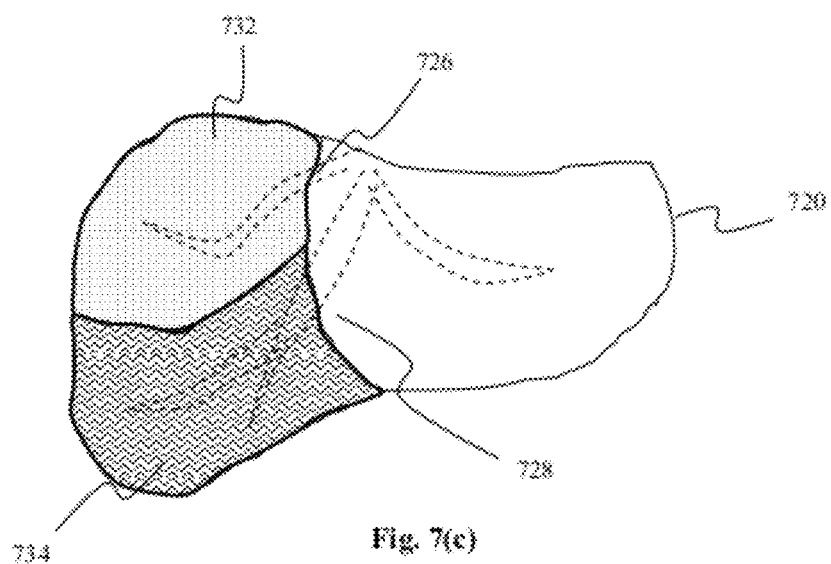
FIG. 7(c) illustrates a functional volume calculation in the predictive cutting of FIG. 7(b), according to an embodiment of the present teaching.

FIG. 7(c) illustrates one example of how the functional volume of an anatomy may be computed. Region 732 is blood drainage support area, the volume of which defines the functional volume of the hepatic vein 726 that has been cut. When the vessel 728 is predicted as being cut, the affected functional volume is indicated by region 734. With this estimation of predictive functional volume of the affected anatomies, the remnant functional volume of the organ may be estimated.

Figure 7D:
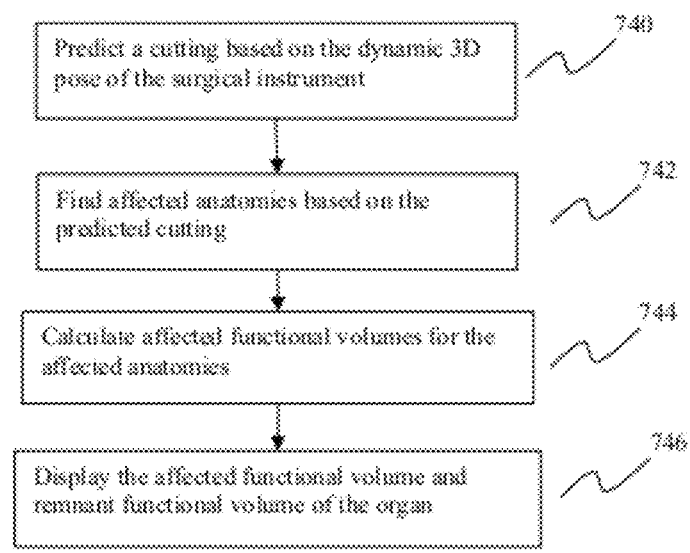
FIG. 7(d) is a flowchart of an exemplary process of the real-time organ function prediction unit, according to an embodiment of the present teaching.

FIG. 7(d) is a flowchart of an exemplary process of the real-time organ function prediction unit 107 in FIG. 7(a), according to one embodiment of the present teaching. At step 740, a cutting may be predicted based on the dynamic 3D pose of the surgical instrument. At step 742, the affected anatomies may be estimated. At step 744, functional volumes related to the affected anatomies may be computed. At step 746, the affected functional volume and the remnant functional volume of the organ may be displayed to surgeons.

Figure 8A:
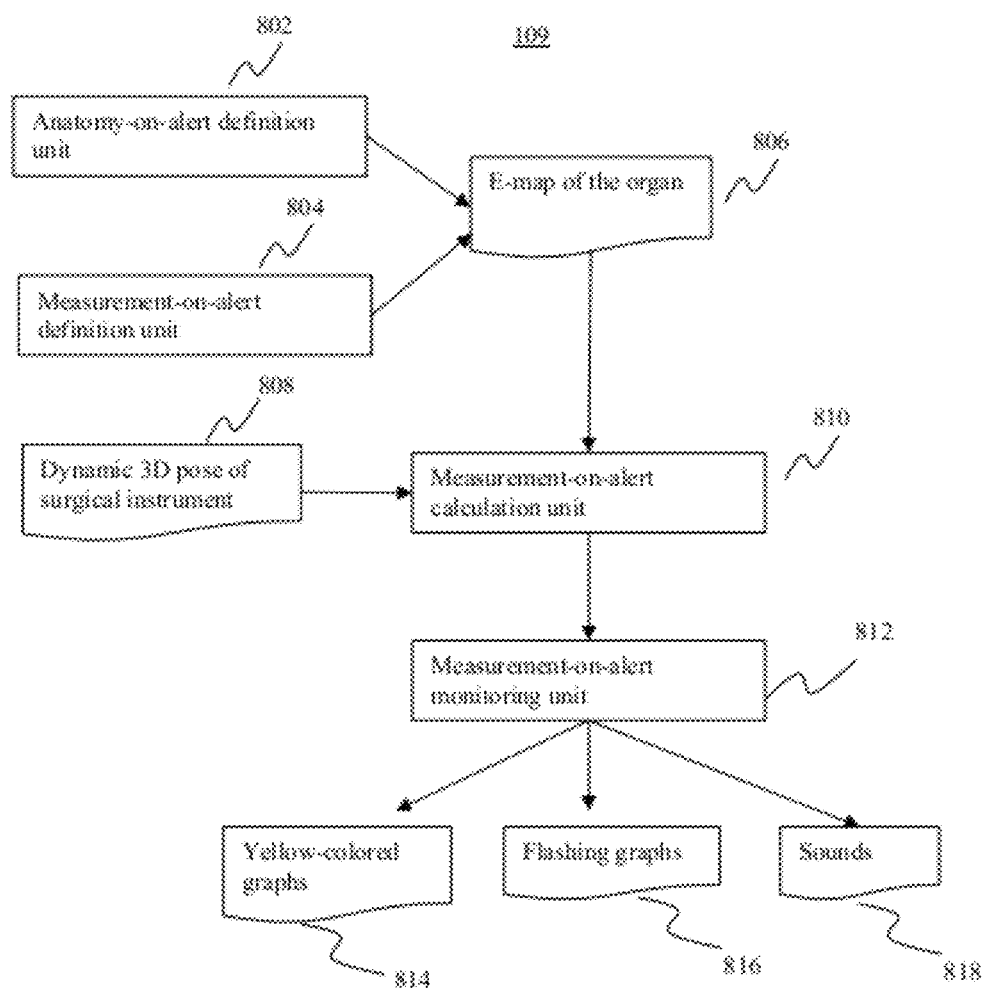
FIG. 8(a) is an exemplary system diagram of a real-time anatomy-on-alert monitoring unit, according to an embodiment of the present teaching.

FIG. 8(a) shows an exemplary system diagram of the real-time anatomy-on-alert monitoring unit 109, according to one embodiment of the present teaching. An anatomy-on-alert definition unit 802 may allow a user to define which anatomies in the E-map 806 may be critical during surgery and need to be monitored. For example, arteries in a liver transplantation are critical anatomies and may need to be avoided in a cutting. Therefore, an artery branch may be defined as an anatomy-on-alert and may be monitored during surgery. The measurement-on-alert definition unit 804 may define which measurements are to be made with respect to the anatomy-on-alerts. As an embodiment of the present teaching, the measurement-on-alert for an artery segment may be defined as the shortest distance from the surgical instrument tip to the artery segment. An anatomy-on-alerts may also be defined as a preplanned surgical path. The corresponding measurement-on-alert may be defined as the distance between the surgical instrument tip and the predefined path. A measurement-on-alert calculation unit 810 may compute predefined measurement-on-alerts, based on the dynamic 3D pose of the surgical instrument 808. A measurement-on-alert monitoring unit 812 may display the measurement-on-alerts in different forms, such as digits or graphs. When the computed measurement-on-alerts are within a warning range, a corresponding warning signal may be issued. For example, when the distance of the surgical instrument to the artery is within a predefined value, or when the distance of the surgical instrument tip to the preplanned surgical path is beyond a predefined value, a warning signal may be issued. The warning signal may be in the form of a yellow-colored graph 814, a flashing graph 816, a warning sound 818, or in any other suitable form.

Figure 8B:
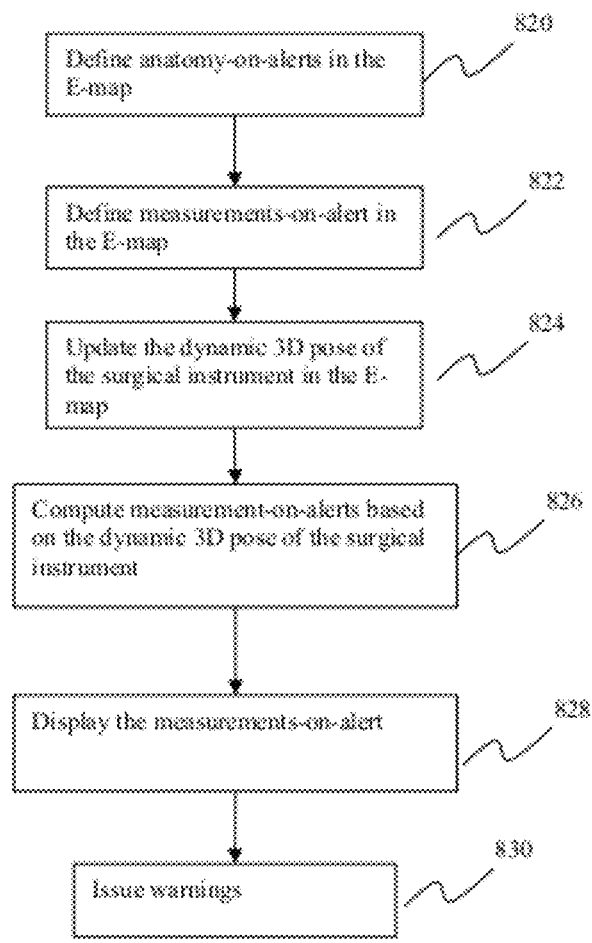
FIG. 8(b) shows a flowchart of an exemplary process of the real-time anatomy-on-alert monitoring unit, according to an embodiment of the present teaching.

FIG. 8(b) is a flowchart of an exemplary process of the real-time anatomy-on-alert monitoring unit 109 in FIG. 8(a), according to one embodiment of the present teaching. At step 820, anatomy-on-alerts may be defined in the E-map of the organ. At step 822, measurement-on-alerts may be defined for the defined anatomy-on-alerts. At step 824, the dynamic 3D pose of the surgical instrument may be updated in the E-map. At step 826, the defined measurement-on-alerts may be computed. The computed measurement-on-alerts may be displayed to surgeons at step 828. A warning signal may be issued at step 830 if the measurement-on-alert falls within the warning range or beyond a predefined value.

Figure 9:
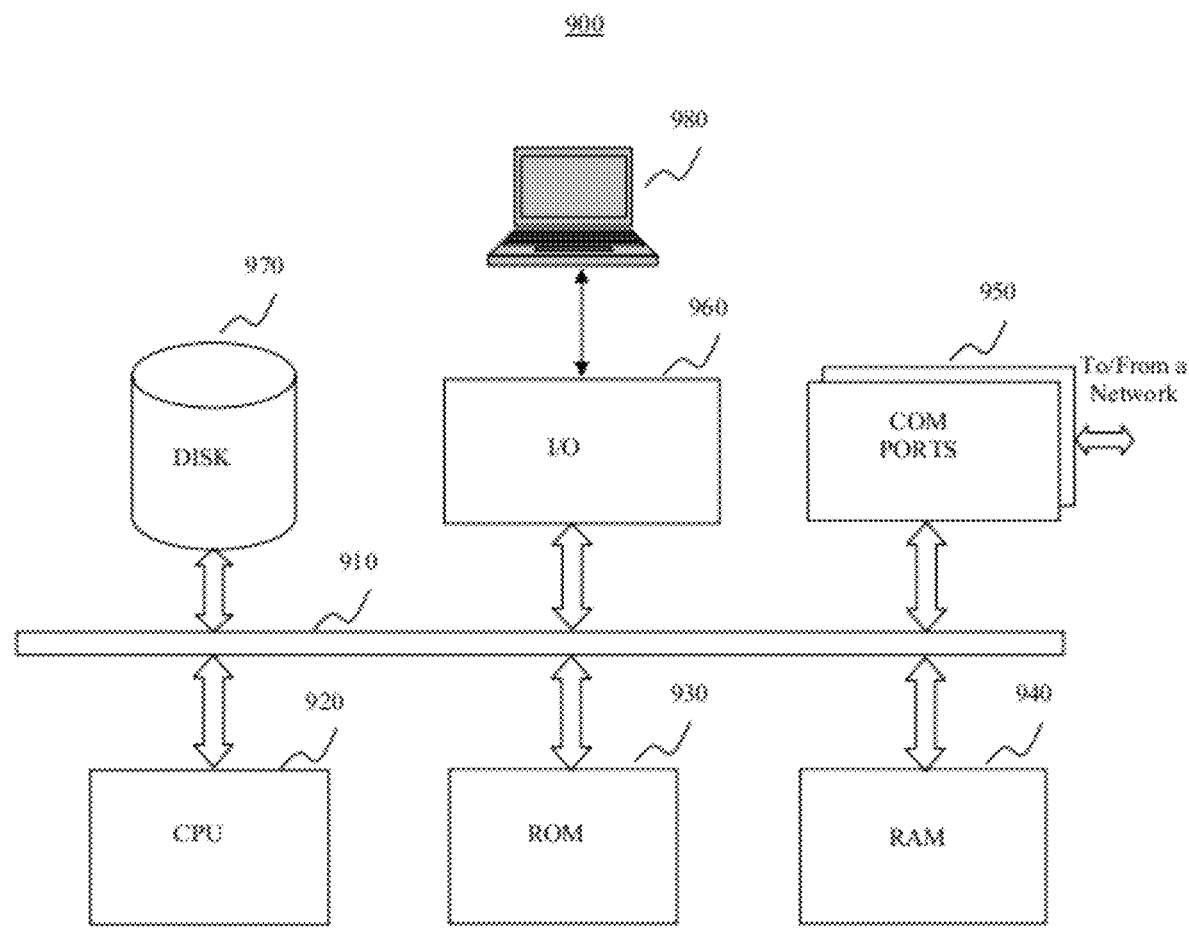
FIG. 9 depicts a general computer architecture on which the present teaching can be implemented.

FIG. 9 depicts a general computer architecture on which the present teaching can be implemented and has a functional block diagram illustration of a computer hardware platform that includes user interface elements. The computer may be a general-purpose computer or a special purpose computer. This computer 900 can be used to implement any components of the real-time surgical procedure assistance system as described herein. Different components of the real-time surgical procedure assistance system 100, e.g., as depicted in FIG. 1(a), can all be implemented on a computer such as computer 900, via its hardware, software program, firmware, or a combination thereof. Although only one such computer is shown, for convenience, the computer functions relating to dynamic relation and event detection may be implemented in a distributed fashion on a number of similar platforms, to distribute the processing load.

The computer 900, for example, includes COM ports 950 connected to and from a network connected thereto to facilitate data communications. The computer 900 also includes a central processing unit (CPU) 920, in the form of one or more processors, for executing program instructions. The exemplary computer platform includes an internal communication bus 910, program storage and data storage of different forms, e.g., disk 970, read only memory (ROM) 930, or random access memory (RAM) 940, for various data files to be processed and/or communicated by the computer, as well as possibly program instructions to be executed by the CPU. The computer 900 also includes an I/O component 960, supporting input/output flows between the computer and other components therein such as user interface elements 980. The computer 900 may also receive programming and data via network communications.

Hence, aspects of the method for real-time surgical procedure assistance, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media may be involved in carrying one or more sequences of one or more instructions to a processor for execution.

Those skilled in the art will recognize that the present teachings are amenable to a variety of modifications and/or enhancements. For example, although the implementation of various components described above may be embodied in a hardware device, it can also be implemented as a software only solution, as a firmware, firmware/software combination, firmware/hardware combination, or a hardware/firmware/software combination.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method implemented on a computer having a processor, a storage, and a communication platform for real-time surgical procedure assistance, comprising:
   receiving, by a tracking unit implemented by the processor, a first set of 3D poses representing positions and orientations of a plurality of 3D points tracked in real-time via a plurality of sensors placed with respect to an organ to which the surgical procedure is applied, wherein the first set of 3D poses can change over time during the surgical procedure;
   retrieving an electronic organ map built for the organ via pre-surgical medical information;
   identifying, by a registration unit implemented by the processor, a second set of 3D poses from the electronic organ map that correspond to the first set of 3D poses by registering each of the plurality of 3D points associated with the first set of 3D poses with a corresponding 3D point from the electronic organ map;
   computing, by the registration unit implemented by the processor, a deformation transformation parameter corresponding to a deformation of the electronic organ map based on the registration between the first set of 3D poses and the second set of 3D poses;
   computing by the registration unit implemented by the processor, a tissue parameter based on actual 3D poses of the plurality of sensors inside the organ and estimated 3D poses of the plurality of sensors inside the organ, wherein the estimated 3D poses are determined based on a function of the computed deformation transformation parameter;
   refining, by the registration unit, propagation of the deformation based on the computed tissue parameter;
   receiving information related to at least one dynamic 3D pose of a surgical instrument which moves during the surgical procedure;
   dynamically estimating a cross section of a portion of the organ predicted to be cut by the surgical instrument during the surgical procedure based on the at least one dynamic 3D pose of the surgical instrument and the deformed electronic organ map, the deformed electronic organ map being projected onto the organ during the surgical process;
   determining an anatomical structure included in the portion of the organ that is affected by a cutting of the surgical instrument during the surgical procedure;
   estimating a functional volume of a remnant portion of the organ corresponding to the anatomical structure, wherein the estimation of the functional volume is dynamically changed with a movement of the surgical instrument during the surgical procedure; and
   displaying the estimated functional volume on a display.

2. The method of claim 1, wherein each of the sensors is capable of detecting its 3D position and orientation.

3. The method of claim 1, wherein the first set of 3D poses represent corresponding 3D points located on the surface of the organ.

4. The method of claim 1, wherein the electronic organ map for the organ is built based on one or more scans of the organ.

5. The method of claim 1, wherein the at least one dynamic 3D pose of the surgical instrument is detected via one or more sensors attached to the surgical instrument.

6. The method of claim 1, wherein the at least one dynamic 3D pose changes when the surgical instrument is in motion.

7. The method of claim 1, further comprising:
computing, automatically, one or more dynamically changing features associated with one or more pre-determined anatomy-based-alerts based on the deformed electronic organ map and the at least one dynamic 3D poses of the surgical instrument, wherein the one or more dynamically changing features further comprise at least one of:
a projection of anatomical structure of the organ rendered on the display with respect to the organ; and
one or more warnings generated based on the at least one dynamic 3D pose of the surgical instrument and the anatomical structure of the organ.

8. The method of claim 1, wherein identifying the second set of 3D poses comprises:
receiving a plurality of user-identified 3D poses of at least some of the plurality of 3D points corresponding to a set of anatomical landmarks of the organ identified by a user;
associating at least one of the plurality of user-identified 3D poses with its corresponding 3D pose of 3D point from the electronic organ map;
receiving a plurality of computer-suggested 3D poses of at least some of the plurality of 3D points corresponding to a set of anatomical landmarks from the electronic organ map suggested by a computer;
associating at least one of the plurality of computer-suggested 3D poses with its corresponding 3D pose of 3D point of the organ; and
registering each 3D point of the organ with a corresponding 3D point from the electronic organ map based on the association between the at least one user-identified 3D pose of the organ and its corresponding 3D pose from the electronic organ map and the association between the at least one computer-suggested 3D pose from the electronic organ map and its corresponding 3D pose of the organ.

9. A machine-readable tangible and non-transitory medium having information for real-time surgical procedure assistance recorded thereon, wherein the information, when read by the machine, causes the machine to perform the following:
receiving, by a tracking unit implemented by the processor, a first set of 3D poses representing positions and orientations of a plurality of 3D points tracked in real-time via a plurality of sensors placed with respect to an organ to which the surgical procedure is applied, wherein the first set of 3D poses can change over time during the surgical procedure;
retrieving an electronic organ map built for the organ via pre-surgical medical information;
identifying, by a registration unit implemented by the processor, a second set of 3D poses from the electronic organ map that correspond to the first set of 3D poses by registering each of the plurality of 3D points associated with the first set of 3D poses with a corresponding 3D point from the electronic organ map;
computing, by the registration unit implemented by the processor, a deformation transformation parameter corresponding to a deformation of the electronic organ map based on the registration between the first set of 3D poses and the second set of 3D poses;
computing by the registration unit implemented by the processor, a tissue parameter based on actual 31D poses of the plurality of sensors inside the organ and estimated 3D poses of the plurality of sensors inside the organ, wherein the estimated 3D poses are determined based on a function of the computed deformation transformation parameter;
refining, by the registration unit, propagation of the deformation based on the computed tissue parameter;
receiving information related to at least one dynamic 3D pose of a surgical instrument which moves during the surgical procedure;
dynamically estimating a cross section of a portion of the organ predicted to be cut by the surgical instrument during the surgical procedure based on the at least one dynamic 3D pose of the surgical instrument and the deformed electronic organ map, the deformed electronic organ map being projected onto the organ during the surgical process;
determining an anatomical structure included in the portion of the organ that is affected by a cutting of the surgical instrument during the surgical procedure;
estimating a functional volume of a remnant portion of the organ corresponding to the anatomical structure, wherein the estimation of the functional volume is dynamically changed with a movement of the surgical instrument during the surgical procedure; and
displaying the estimated functional volume on a display.

10. The medium of claim 9, wherein each of the sensors is capable of detecting its 3D position and orientation.

11. The medium of claim 9, wherein the first set of 3D poses represent corresponding 3D points located on the surface of the organ.

12. The medium of claim 9, wherein the electronic organ map for the organ is built based on one or more scans of the organ.

13. The medium of claim 9, wherein the at least one dynamic 3D pose of the surgical instrument is detected via one or more sensors attached to the surgical instrument.

14. The medium of claim 9, wherein the at least one dynamic 3D pose changes when the surgical instrument is in motion.

15. The medium of claim 9, further comprising:
computing, automatically, one or more dynamically changing features associated with one or more pre-determined anatomy-based-alerts based on the deformed electronic organ map and the at least one dynamic 3D poses of the surgical instrument, wherein the one or more dynamically changing features further comprise at least one of:
a projection of anatomical structure of the organ rendered on the display with respect to the organ; and
one or more warnings generated based on the at least one dynamic 3D pose of the surgical instrument and the anatomical structure of the organ.

16. The medium of claim 9, wherein identifying the second set of 3D poses comprises:
receiving a plurality of user-identified 3D poses of at least some of the plurality of 3D points corresponding to a set of anatomical landmarks of the organ identified by a user;

associating at least one of the plurality of user-identified 3D poses with its corresponding 3D pose from the electronic organ map;

receiving a plurality of computer-suggested 3D poses of at least some of the plurality of 3D points corresponding to a set of anatomical landmarks from the electronic organ map suggested by a computer;

associating at least one of the plurality of computer-suggested 3D poses with its corresponding 3D pose of the organ; and registering each 3D point of the organ with a corresponding 3D point from the electronic organ map based on the association between the at least one user-identified 3D pose of the organ and its corresponding 3D pose from the electronic organ map and the association between the at least one computer-suggested 3D pose from the electronic organ map and its corresponding 3D pose of the organ.

17. The method of claim 1, wherein the anatomical structure comprises a blood vessel.

18. The medium of claim 9, wherein the anatomical structure comprises a blood vessel.

19. The method of claim 1, wherein the function is a Spline function.

20. A system comprising:
one or more processors configured to:
receive a first set of 3D poses representing positions and orientations of a plurality of 3D points tracked in real-time via a plurality of sensors placed with respect to an organ to which the surgical procedure is applied, wherein the first set of 3D poses can change over time during the surgical procedure, retrieve an electronic organ map built for the organ via pre-surgical medical information, identify a second set of 3D poses from the electronic organ map that correspond to the first set of 3D poses by registering each of the plurality of 3D points associated with the first set of 3D poses with a corresponding 3D point from the electronic organ map, compute a deformation transformation parameter corresponding to a deformation of the electronic organ map based on the registration between the first set of 3D poses and the second set of 3D poses, compute a tissue parameter based on actual 31D poses of the plurality of sensors inside the organ and estimated 3D poses of the plurality of sensors inside the organ, wherein the estimated 3D poses are determined based on a function of the computed deformation transformation parameter, refine propagation of the deformation based on the computed tissue parameter, receive information related to at least one dynamic 3D pose of a surgical instrument which moves during the surgical procedure, estimate dynamically, a cross section of a portion of the organ predicted to be cut by the surgical instrument during the surgical procedure based on the at least one dynamic 3D pose of the surgical instrument and the deformed electronic organ map, the deformed electronic organ map being projected onto the organ during the surgical procedure, determine an anatomical structure included in the portion of the organ drat is affected by a cutting of the surgical instrument during the surgical procedure, estimate a functional volume of a remnant portion of the organ corresponding to the anatomical structure, wherein the estimation of the functional volume is dynamically changed with a movement of the surgical instrument during the surgical procedure, and display the estimated functional volume on a display.

* * * * *